(12) United States Patent
Nakaoka et al.

(10) Patent No.: US 12,329,620 B2
(45) Date of Patent: Jun. 17, 2025

(54) DISPOSABLE DIAPER

(71) Applicant: LIVEDO CORPORATION, Ehime (JP)

(72) Inventors: Kenji Nakaoka, Tokushima (JP); Yuki Takahashi, Tokushima (JP)

(73) Assignee: LIVEDO CORPORATION, Ehime (JP)

( * ) Notice: Subject to any disclaimer, the term of this patent is extended or adjusted under 35 U.S.C. 154(b) by 898 days.

(21) Appl. No.: 17/283,141

(22) PCT Filed: Jun. 25, 2019

(86) PCT No.: PCT/JP2019/025126
§ 371 (c)(1),
(2) Date: Apr. 6, 2021

(87) PCT Pub. No.: WO2020/075348
PCT Pub. Date: Apr. 16, 2020

(65) Prior Publication Data
US 2021/0386598 A1    Dec. 16, 2021

(30) Foreign Application Priority Data
Oct. 12, 2018 (JP) .................................. 2018-193233

(51) Int. Cl.
*A61F 13/49* (2006.01)
*A61F 13/539* (2006.01)

(52) U.S. Cl.
CPC ...... *A61F 13/49017* (2013.01); *A61F 13/539* (2013.01)

(58) Field of Classification Search
CPC .......... A61F 13/49012; A61F 13/49017; A61F 13/51478; A61F 13/539; A61F 2013/49025; A61F 2013/53908; A61F 2013/53925
See application file for complete search history.

(56) References Cited

U.S. PATENT DOCUMENTS

| | | | |
|---|---|---|---|
| 6,602,238 B2 * | 8/2003 | Takei | A61F 13/49019 604/385.03 |
| 6,635,798 B1 * | 10/2003 | Yoshioka | A61F 13/15203 604/385.01 |

(Continued)

FOREIGN PATENT DOCUMENTS

| | | |
|---|---|---|
| JP | 8-280739 | 10/1996 |
| JP | 2004-49763 | 2/2004 |

(Continued)

OTHER PUBLICATIONS

International Search Report issued Jul. 30, 2019 in International (PCT) Application No. PCT/JP2019/025126.

(Continued)

*Primary Examiner* — Catharine L Anderson
(74) *Attorney, Agent, or Firm* — Wenderoth, Lind & Ponack, L.L.P.

(57) ABSTRACT

A disposable diaper in which an absorbent body (7) is provided on a crotch part of a pants-shaped exterior member (2), wherein the absorbent body (7) is adhered to a skin-facing side of the exterior member (2) at a first adhering region (14), an inner sheet (5) and an outer sheet (6) of the exterior member (2) are adhered to each other at a second adhering region (16), the second adhering region (16) includes a second middle adhering region (16M) provided at the crotch part, a second front adhering region (16F) located anterior thereto and a second rear adhering region (16B) located posterior thereto, the second front adhering region (16F) and/or the second rear adhering region (16B) is provided intermittently from one side edge to the other side edge, with respect to the width direction, of the absorbent body (7), and a second front non-adhering region (17F) and/or a second rear non-adhering region (17B) is formed at a portion which the absorbent body (7) is overlapped with (Continued)

and is provided so as to overlap with one side edge and the other side edge, with respect to the width direction, of the first adhering region (14).

12 Claims, 7 Drawing Sheets (56) References Cited

U.S. PATENT DOCUMENTS

| | | | |
|---|---|---|---|
| 7,217,261 B2 * | 5/2007 | Otsubo | A61F 13/49011 604/385.29 |
| 7,329,245 B2 * | 2/2008 | Torigoshi | 604/385.27 |
| 7,727,214 B2 * | 6/2010 | Torigoshi | A61F 13/4942 604/385.24 |
| 8,372,053 B2 * | 2/2013 | Shimada | A61F 13/496 604/385.27 |
| 8,382,733 B2 | 2/2013 | Okawa et al. | |
| 8,449,515 B2 * | 5/2013 | Saito | A61F 13/49017 604/385.27 |
| 9,801,764 B2 | 10/2017 | Arayama et al. | |
| 10,092,457 B2 * | 10/2018 | Ishikawa | A61F 13/49012 |
| 11,291,592 B2 * | 4/2022 | Takaishi | A61F 13/49011 |
| 11,925,538 B2 | 3/2024 | Andrews et al. | |
| 2003/0212376 A1 | 11/2003 | Walter et al. | |
| 2009/0299319 A1 | 12/2009 | Takahashi et al. | |
| 2017/0079854 A1 | 3/2017 | Butler et al. | |
| 2019/0076304 A1 | 3/2019 | Borrero et al. | |
| 2019/0290505 A1 | 9/2019 | Varona et al. | |
| 2020/0078231 A1 | 3/2020 | Arora et al. | |
| 2021/0386598 A1 | 12/2021 | Nakaoka et al. | |
| 2021/0386600 A1 * | 12/2021 | Nakaoka | A61F 13/539 |
| 2022/0142830 A1 | 5/2022 | Lambertz et al. | |

FOREIGN PATENT DOCUMENTS

| | | |
|---|---|---|
| JP | 2004-298395 | 10/2004 |
| JP | 2005-87622 | 4/2005 |
| JP | 2008-228834 | 10/2008 |
| JP | 2009-189621 | 8/2009 |
| JP | 2013-188379 | 9/2013 |
| JP | 2014-180346 | 9/2014 |

OTHER PUBLICATIONS

International Search Report issued Jul. 30, 2019 in International (PCT) Application No. PCT/JP2019/025127.

Office Action issued Mar. 15, 2022 in corresponding Japanese Patent Application No. 2018-193233, with English language translation.

\* cited by examiner

DISPOSABLE DIAPER

TECHNICAL FIELD

The present invention relates to a pants-type disposable diaper.

BACKGROUND ART

Conventionally, disposable diapers comprising an exterior member that is formed in a pants shape and an absorbent body provided on a crotch part of the exterior member and includes a top sheet, a back sheet and an absorber provided therebetween have been known (for example, Patent Literatures 1 to 6). Patent Literature 6 discloses a disposable diaper in which a leg circumference elastic material is fixed between a plurality of sheets constituting the exterior member along left and right leg openings of the exterior member, wherein an adhesive is applied to at least three block-shaped regions formed by dividing an outer periphery of each of a left leg opening forming portion and a right leg opening forming portion, and the leg circumference elastic material is disposed on an application area to which the adhesive is applied in a stretched state so as to extend along each of the left leg opening forming portion and the right leg opening forming portion.

CITATION LIST

Patent Literature

Patent Literature 1
   Japanese Unexamined Laid-open Patent Application Publication No. H08-280739
Patent Literature 2
   Japanese Unexamined Laid-open Patent Application Publication No. 2004-049763
Patent Literature 3
   Japanese Unexamined Laid-open Patent Application Publication No. 2004-298395
Patent Literature 4
   Japanese Unexamined Laid-open Patent Application Publication No. 2005-087622
Patent Literature 5
   Japanese Unexamined Laid-open Patent Application Publication No. 2014-180346
Patent Literature 6
   Japanese Unexamined Laid-open Patent Application Publication No. 2009-189621

SUMMARY OF INVENTION

Technical Problem

Since disposable diapers are worn for a relatively long time, it is desirable that sweat or moisture generated from a wearer is suitably discharged to the outside of the diaper for improving wearing feeling. In particular, in a disposable diaper in which an absorbent body is provided on a crotch part of a pants-shaped exterior member, air permeability at a portion where the absorbent body is overlapped with the exterior member tends to decrease. The present invention has been made in view of the above circumstances, and an object of the present invention is to provide a disposable diaper which is excellent in air permeability.

Solution to Problem

The disposable diaper of the present invention which solves the above problems is a diaper comprising: an exterior member that has a front body part, a rear body part and a crotch part positioned therebetween and is formed into a pants shape having a waist opening and a pair of leg openings by joining the front body part and the rear body part; and an absorbent body that is provided at least on the crotch part of the exterior member and includes a top sheet, a back sheet and an absorber provided therebetween; wherein: the exterior member includes an inner sheet and an outer sheet; a front leg elastic member extending across the crotch part and along a front side of an edge of the leg opening and a rear leg elastic member extending across the crotch part and along a rear side of the edge of the leg opening are provided between the inner sheet and the outer sheet; the absorbent body is adhered to a skin-facing side of the exterior member at a first adhering region; the inner sheet and the outer sheet are adhered to each other at a second adhering region, the second adhering region includes a second middle adhering region provided at the crotch part, a second front adhering region located anterior to the second middle adhering region and a second rear adhering region located posterior to the second middle adhering region, and the front leg elastic member and the rear leg elastic member are disposed so as to extend across the crotch part in the second middle adhering region; the second middle adhering region is provided so that at least a part thereof overlaps with the first adhering region and is provided continuously from one side edge to the other side edge of the absorbent body in the width direction; and the second front adhering region is provided so as to satisfy the following requirement A and/or the second rear adhering region is provided so as to satisfy the following requirement B.

(Requirement A) The second front adhering region is provided so that at least a part thereof overlaps with the first adhering region and is provided intermittently from one side edge to the other side edge, with respect to the width direction, of the absorbent body, whereby a second front non-adhering region in which the inner sheet and the outer sheet are not adhered to each other is formed at a portion which the absorbent body is overlapped with on a front side of the second middle adhering region; and the second front adhering region is provided so as to overlap with one side edge and the other side edge, with respect to the width direction, of the first adhering region.

(Requirement B) The second rear adhering region is provided so that at least a part thereof overlaps with the first adhering region and is provided intermittently from one side edge to the other side edge, with respect to the width direction, of the absorbent body, whereby a second rear non-adhering region in which the inner sheet and the outer sheet are not adhered to each other is formed at a portion which the absorbent body is overlapped with on a rear side of the second middle adhering region; and the second rear adhering region is provided so as to overlap with one side edge and the other side edge, with respect to the width direction, of the first adhering region.

In the disposable diaper of the present invention, the absorbent body is adhered to a skin-facing side of the exterior member at the first adhering region, and the inner sheet and the outer sheet of the exterior member are adhered to each other at the second front adhering region, the second rear adhering region and the second middle adhering region provided therebetween. At this time, the second front adhering region and/or the second rear adhering region are provided intermittently in the width direction, whereby the second front non-adhering region and/or the second rear non-adhering region in which the inner sheet and the outer sheet of the exterior member are not adhered to each other is formed at a portion which the absorbent body is overlapped with. Therefore, air permeability of the exterior member is increased, and sweat or moisture generated from a wearer is easily discharged to the outside of the diaper. Meanwhile, since the second middle adhering region is provided so as to overlap with the first adhering region, and the second front adhering region and/or the second rear adhering region is provided so as to overlap with one side edge and the other side edge, with respect to the width direction, of the first adhering region, the position of the absorbent body relative to the exterior member is suitably settled via the first adhering region and the second adhering region, and the absorbent body is less likely to shift at a wearer's crotch. Therefore, wearing feeling of the disposable diaper can be improved.

It is preferable that the front leg elastic member and the rear leg elastic member are provided so as to extend intermittently across the crotch part in the second middle adhering region. When the front leg elastic member and the rear leg elastic member are provided in this manner, the absorbent body is less likely to be distorted by contraction force of the front leg elastic member and the rear leg elastic member, and fittability of the absorbent body to a wearer's crotch can be improved.

It is preferable that the second middle adhering region is provided so as to extend outward in the width direction from the one side edge and the other side edge, with respect to the width direction, of the absorbent body to an outer edge of the exterior member. By providing the second middle adhering region in this manner, the parts of the front leg elastic member and the rear leg elastic member that cross the crotch part and extend along the edge of the leg opening are adhered and fixed to the inner sheet and/or the outer sheet.

It is preferable that the second front adhering region is provided so as to extend forward of a front end of the absorbent body, and/or the second rear adhering region is provided so as to extend rearward of a rear end of the absorbent body. When the second front adhering region and/or the second rear adhering region are provided in this manner, the position of the end portion of the absorbent body in the front-rear direction is suitably settled relative to the exterior member, and the absorbent body is less likely to shift relative to the exterior member over a wide range in the front-rear direction.

It is preferable that the second front adhering region is provided so as to extend outward in the width direction from the one side edge and the other side edge, with respect to the width direction, of the absorbent body and overlap with the front leg elastic member, and extend forward of the front leg elastic member; and/or the second rear adhering region is provided so as to extend outward in the width direction from the one side edge and the other side edge, with respect to the width direction, of the absorbent body and overlap with the rear leg elastic member, and extend rearward of the rear leg elastic member. By providing the second front adhering region and/or the second rear adhering region in this manner, the part of the front leg elastic member and/or the rear leg elastic member that extends along the edge of the leg opening is adhered and fixed to the inner sheet and/or the outer sheet.

It is preferable that a body elastic member extending in the width direction is provided between the inner sheet and the outer sheet on the front body part and the rear body part, and the second front adhering region and/or the second rear adhering region is provided apart from the body elastic member, whereby a non-adhering region in which the inner sheet and the outer sheet are not adhered to each other is formed between the second front adhering region and the body elastic member and/or between the second rear adhering region and the body elastic member. By providing the non-adhering region in this manner, moisture accumulated in the second front non-adhering region or the second rear non-adhering region is easily discharged to the outside of the diaper.

With regard to the relationship with the first adhering region, the second front non-adhering region and the second rear non-adhering region are preferably provided as follows. That is, it is preferable that: a value of $W_{A2}/W_{A1}$ is 0.15 or more and 0.90 or less, provided that a length from one side edge to the other side edge, with respect to the width direction, of a portion where the first adhering region overlaps with the second front adhering region is $W_{A1}$ and a length of the second front non-adhering region in the width direction is $W_{A2}$; and/or a value of $W_{B2}/W_{B1}$ is 0.15 or more and 0.90 or less, provided that a length from one side edge to the other side edge, with respect to the width direction, of a portion where the first adhering region overlaps with the second rear adhering region is $W_{B1}$ and a length of the second rear non-adhering region in the width direction is $W_{B2}$.

It is preferable that a length of the second front non-adhering region in the width direction is longer than a length of the second rear non-adhering region in the width direction. Thereby, air permeability on a front side of the diaper, in which more urine tends to be collected, can be increased.

It is preferable that the second front adhering region and/or the second rear adhering region has higher bending resistance than the second middle adhering region. Thereby, the crotch part of the exterior member is formed softly, and wearing feeling of the disposable diaper can be improved.

It is preferable that the first adhering region is provided continuously in the width direction so as to extend across the plurality of second front adhering regions provided intermittently in the width direction, and/or the first adhering region is provided continuously in the width direction so as to extend across the plurality of second rear adhering regions provided intermittently in the width direction. In this manner, when the first adhering region is continuously provided in the width direction and is provided so as to extend across the plurality of second front adhering regions and/or the second rear adhering regions that is provided intermittently in the width direction, the absorbent body is less likely to shift relative to the exterior member and it becomes easy to set the absorbent body at an intended position at a wearer's crotch when wearing the diaper.

It is also preferable that the first adhering region is provided intermittently in the width direction, whereby a first non-adhering region in which the absorbent body is not adhered to the exterior member is formed between the adjacent first adhering regions, and the second front non-adhering region and/or the second rear non-adhering region is provided so as to overlap with the first non-adhering region. In this case, air permeability of the disposable diaper can be further increased.

Advantageous Effects of Invention

In the disposable diaper of the present invention, the absorbent body is adhered to a skin-facing side of the exterior member at the first adhering region, and the inner sheet and the outer sheet of the exterior member are adhered to each other at the second front adhering region, the second rear adhering region and the second middle adhering region provided therebetween. At this time, the second front adhering region and/or the second rear adhering region are provided intermittently in the width direction, whereby a non-adhering region in which the inner sheet and the outer sheet of the exterior member are not adhered to each other is formed at a portion which the absorbent body is overlapped with. Therefore, air permeability of the exterior member is increased, and sweat or moisture generated from a wearer is easily discharged to the outside of the diaper. Meanwhile, since the second middle adhering region is provided so as to overlap with the first adhering region, and the second front adhering region and/or the second rear adhering region is provided so as to overlap with one side edge and the other side edge, with respect to the width direction, of the first adhering region, it becomes easy to suitably settle the position of the absorbent body relative to the exterior member via the first adhering region and the second adhering region, and therefore, wearing feeling of the disposable diaper can be improved.

DESCRIPTION OF THE PREFERRED EMBODIMENTS

Figure 1:
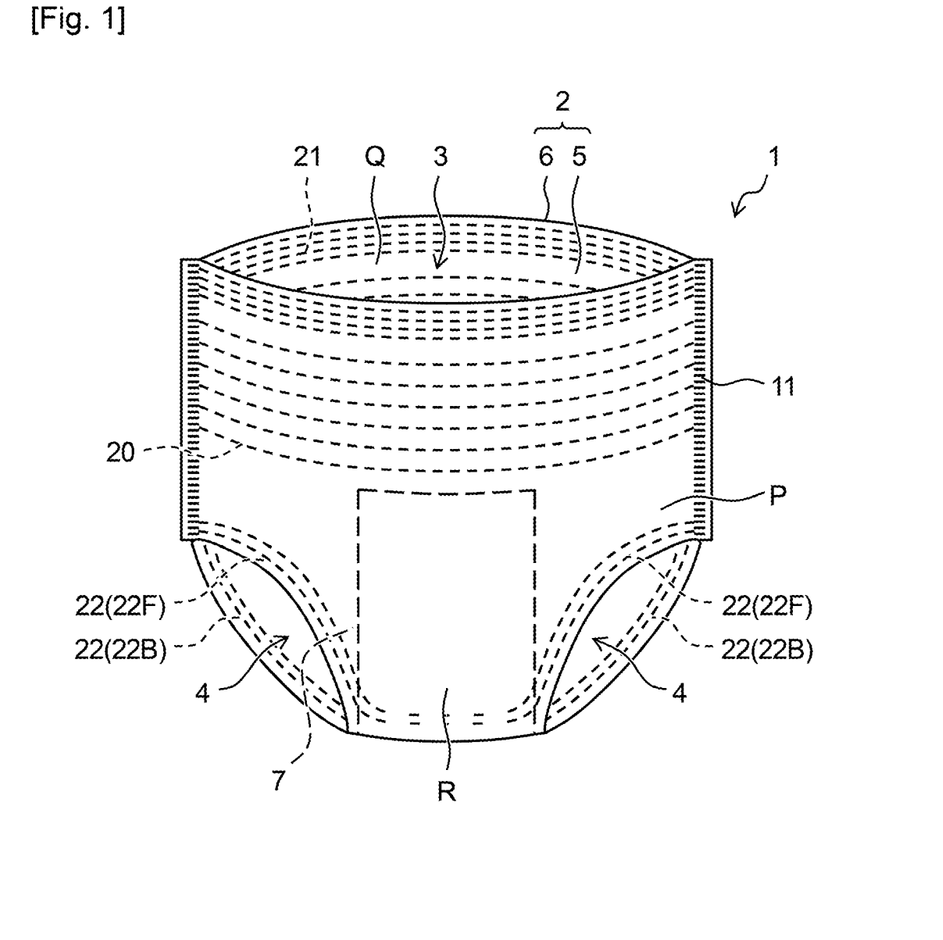
FIG. 1 shows a perspective view of a disposable diaper.
Figure 2:
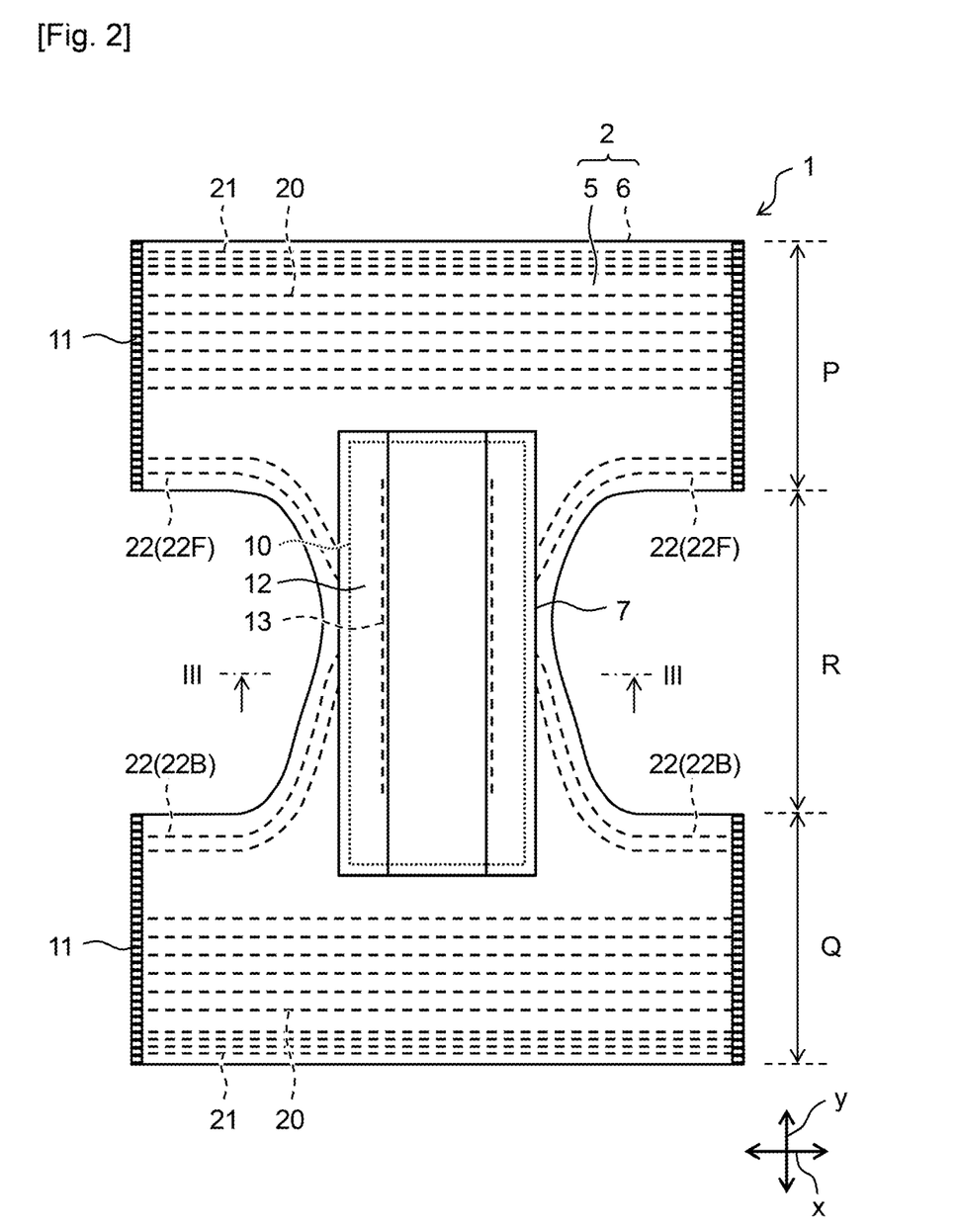
FIG. 2 shows a plan view of the disposable diaper shown in FIG. 1, as viewed from a skin-facing side thereof, in a developed state where a front body part and a rear body part are disjoined.
Figure 3:
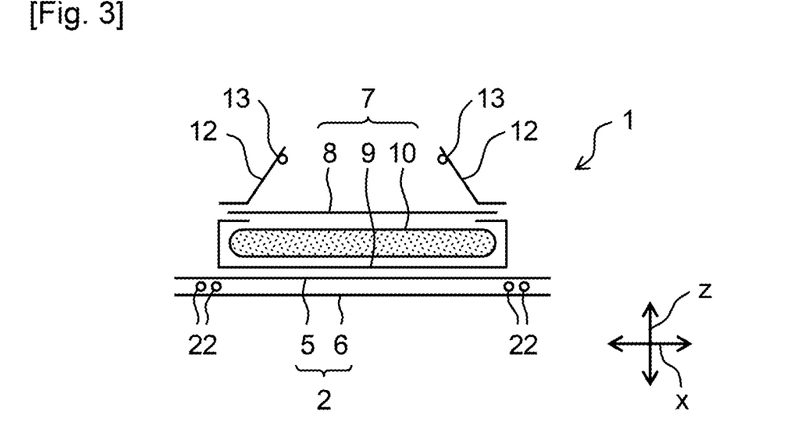
FIG. 3 shows a cross-sectional view along a line III-III of the disposable diaper shown in FIG. 2.

A disposable diaper of the present invention is explained with reference to the drawings. However, the present invention is not limited to the embodiments shown in the drawings. FIGS. 1 to 3 show an example of a disposable diaper of the present invention. FIG. 1 shows a perspective view of a disposable diaper, FIG. 2 shows a plan view of the disposable diaper shown in FIG. 1, as viewed from a skin-facing side thereof, in a developed state where a front body part and a rear body part are disjoined, and FIG. 3 shows a cross-sectional view along a line III-III of the disposable diaper shown in FIG. 2. In the drawings, an arrow x represents a width direction, an arrow y represents a front-rear direction, and the direction perpendicular to the surface formed by the arrows x and y represents a thickness direction z.

A disposable diaper 1 comprises an exterior member 2 having a front body part P, a rear body part Q and a crotch part R positioned therebetween. The exterior member 2 is formed into a pants shape having a waist opening 3 and a pair of leg openings 4 by joining the front body part P and the rear body part Q. The waist opening 3 is an opening through which a wearer's trunk is put, and the leg opening 4 is an opening through which a wearer's leg is put.

In the exterior member 2, the front body part P corresponds to a part applied to an abdomen side of a wearer in wearing the diaper, and the rear body part Q corresponds to a part applied to a back side of a wearer in wearing the diaper. The front body part P and the rear body part Q are joined to each other on both sides in the width direction x in a state of being formed into a pants shape. The crotch part R is positioned between the front body part P and the rear body part Q, and corresponds to a part applied to a crotch of a wearer. The crotch part R is located in the middle of the exterior member 2 when the exterior member 2 is divided into three in the front-rear direction y, and is not joined to each other on both sides in the width direction x in a state of being formed into a pants shape. The exterior member 2 is formed into a pants shape by joining the front body part P and the rear body part Q at side joint parts 11 on both sides in the width direction x.

In the disposable diaper 1, the front-rear direction y means a direction extending from the front body part P to the rear body part Q, and corresponds to a front-rear direction in a wearer's crotch when the diaper is worn. The width direction x corresponds to a left-right direction of a wearer when the diaper is worn. A skin-facing side of the disposable diaper means a side facing a wearer's skin when the diaper is worn, and an outer side of the disposable diaper means a side facing away from the wearer when the diaper is worn.

An absorbent body 7 is provided on the crotch part R of the exterior member 2. The absorbent body 7 comprises a top sheet 8, a back sheet 9 and an absorber 10 disposed therebetween (see FIG. 3). The top sheet 8 is a sheet located on a wearer's side when the diaper is worn, and is provided on the skin-facing side of the absorber 10. The top sheet 8 is preferably liquid-permeable. The back sheet 9 is a sheet located on a side opposite to a wearer when the diaper is worn, and is provided on the outer side of the absorber 10. The back sheet 9 is preferably liquid-impermeable. Urine and the like excreted from a wearer passes through the top sheet 8 and is stored by the absorber 10, and the back sheet 9 prevents the excrement from leaking to the outside.

As the liquid-permeable top sheet, a nonwoven fabric formed from hydrophilic fibers such as cellulose, rayon and cotton, a nonwoven fabric which is formed from hydrophobic fibers such as polyolefin (e.g., polypropylene, polyethylene), polyester (e.g., PET) and polyamide (e.g., nylon), and whose surface is hydrophilized with a surfactant, or the like can be used, for example. As the top sheet, a woven fabric, a knitted fabric, a plastic film having holes or the like may be also used.

As the liquid-impermeable back sheet, a nonwoven fabric formed from hydrophobic fibers such as polyolefin (e.g., polypropylene, polyethylene), polyester (e.g., PET) and polyamide (e.g., nylon), a plastic film, or the like can be used, for example. The back sheet may be composed of a laminate of two or more sheets, and for example, a laminate of a non-woven fabric and a plastic film may be used. In this case, the sheets constituting the laminate may have the same size or different sizes from each other. The back sheet may be liquid-impermeable and moisture-permeable.

The absorber is not particularly restricted as long as it contains an absorbent material which is able to absorb excrement such as urine. As the absorber, a shaped product of an absorbent material, which is formed into a certain shape, may be used. The absorber may be wrapped with a cover sheet such as a paper (e.g., a tissue paper and a thin paper) and a liquid-permeable nonwoven fabric. Examples of the absorbent material include, for example, a hydrophilic fiber such as a pulp fiber, and an absorbent polymer such as a polyacrylic absorbent polymer, a polyasparaginic absorbent polymer, a cellulosic absorbent polymer, and a stark-acrylonitrile absorbent polymer. The absorbent material may include a thermal fusion fiber such as a polyolefin (e.g., polyethylene and polypropylene) fiber, a polyester (e.g., PET) fiber and a polyamide (e.g., nylon) fiber. These thermal fusion fibers may be hydrophilized with a surfactant or the like to increase affinity with bodily fluid such as urine. The absorbent material preferably includes at least an absorbent polymer in view of enhancing absorption capacity.

The absorber may be an absorbent sheet which is configured so as to contain an absorbent polymer but not contain a pulp fiber between nonwoven fabric sheets. The thus configured absorbent sheet manner enables having high absorption capacity since it contains an absorbent polymer between nonwoven fabric sheets, while it can be formed thin without being bulky since it does not contain a pulp fiber between nonwoven fabric sheets.

In the absorber, an absorbent fiber may be used as the absorbent material. Also in this case, the absorber is formed thin without being bulky. Examples of the absorbent fiber include a fiber having a protonated carboxyl group or a carboxylate group. The absorbent fiber can be obtained by, for example, hydrolyzing an acrylic fiber, thereby converting a nitrile group contained in the acrylic fiber to a carboxylic group. The carboxyl group contained in the absorbent fiber preferably forms an alkaline metal salt or an ammonium salt. The absorbent fiber also can be prepared by immersing a hydrophilic fiber in acrylic acid to deposit acrylic acid on the surface of the fiber.

The shape (planar shape) of the absorber 10 is not particularly limited. Examples of the shape of the absorber 10 include, for example, a substantially rectangular shape, an hourglass shape, a gourd shape, a battledore shape, and the like. In the drawing, the absorber 10 is formed in a substantially rectangular shape.

It is preferable that the absorbent body 7 is provided with rising flaps 12 on both sides in the width direction x on a skin-facing side (see FIGS. 2 and 3). The rising flap 12 enables preventing leakage of excrement such as urine. The rising flap 12 is preferably provided with a rising elastic member 13 at an upper end part thereof in its standing state (an end part on a wearer's side). The rising flap 12 is promoted to stand up by contractive force of the rising elastic member 13.

The exterior member 2 comprises an inner sheet 5 disposed on a skin-facing side thereof and an outer sheet 6 disposed on an outer side thereof. The absorbent body 7 is provided on the skin-facing side of the inner sheet 5. The outer sheet 6 is provided so that its outer surface faces the outside of the diaper. The inner sheet 5 and the outer sheet 6 are respectively configured to have the front body part P, the rear body part Q and the crotch part R. The inner sheet 5 and the outer sheet 6 may be liquid-permeable or liquid-impermeable, and a sheet material that may be used for the top sheet 8 or the back sheet 9 can be used. The inner sheet 5 and the outer sheet 6 are preferably moisture-permeable, whereby wearing feeling of the exterior member 2 can be improved.

In the case where a nonwoven fabric is used as a sheet material for the top sheet, the back sheet, the outer sheet, the inner sheet or the like described above, a spunbonded nonwoven fabric, an air-through nonwoven fabric, a point-bonded nonwoven fabric, a meltblown nonwoven fabric, an SMS nonwoven fabric or the like is preferably used as the nonwoven fabric, that makes it easy to obtain a thin and durable sheet.

In the exterior member 2, a leg elastic member 22 is provided between the inner sheet 5 and the outer sheet 6 along an edge of the leg opening 4. The leg elastic member 22 includes a front leg elastic member 22F disposed so as to extend across the crotch part R and along a front side of the edge of the leg opening 4 and a rear leg elastic member 22B disposed so as to extend across the crotch part R and along a rear side of the edge of the leg opening 4. The front leg elastic member 22F and the rear leg elastic member 22B gives elastic members disposed along almost the entire circumference of the edge of the leg opening 4, thereby forming leg-gathers around a wearer's leg, and leakage of urine and the like from the crotch is prevented. In the drawings, the front leg elastic member 22F and the rear leg elastic member 22B are disposed separately from each other, however, the front leg elastic member 22F and the rear leg elastic member 22B may be disposed in contact with each other or disposed so as to intersect with each other.

It is preferable that a plurality of body elastic members 20 extending in the width direction x are provided between the outer sheet 5 and the inner sheet 6 on the front body part P and the rear body part Q of the exterior member 2. The body elastic members 20 are disposed between the waist opening 3 and the leg opening 4. By disposing the body elastic member 20, fittability around a wearer's trunk can be enhanced. Among the body elastic members 20, elastic members arranged at narrow intervals in the front-rear direction y along the edge of the waist opening 3 may be provided as waist elastic members 21, and thereby, waist gathers around a wearer's waist are formed and leakage of excrement such as urine from the back side or the abdomen side is prevented. In the FIGS. 1 and 2, the waist elastic members 21 are provided at a narrower interval in the front-rear direction y than the body elastic members 20.

The exterior member 2 may be folded back along the edge of the waist opening 3. For example, the outer sheet 6 may be folded back toward the inner sheet 5 at the edge of the waist opening 3 of the exterior member 2 (not shown). In this case, the waist elastic member 21 may be disposed between the folded outer sheets 6 and adhered to the outer sheet 6.

As each elastic member provided in the disposable diaper 1, elastic materials such as a polyurethane thread, a polyurethane film, a natural rubber and the like, that are generally used for disposable diapers, can be used. Each elastic member is preferably fixed to the diaper in a stretched state, and is preferably fixed with an adhesive such as a hot-melt adhesive. For example, a polyurethane thread having a fineness of 40 dtex to 1,240 dtex is stretched at a ratio of 1.1 to 5.0 times and is disposed to be fixed. As the adhesive, a rubber hot-melt adhesive is preferably used. Regarding the above-described ratio, an unexpanded state is defined as 1.0 time.

The absorbent body 7 is provided at least on the crotch part R of the skin-facing side of the exterior member 2, and preferably further extends to the front body part P and/or the rear body part Q. The absorbent body 7 may be formed into, for example, a substantially hourglass shape or a substantially rectangular shape.

Figure 4:
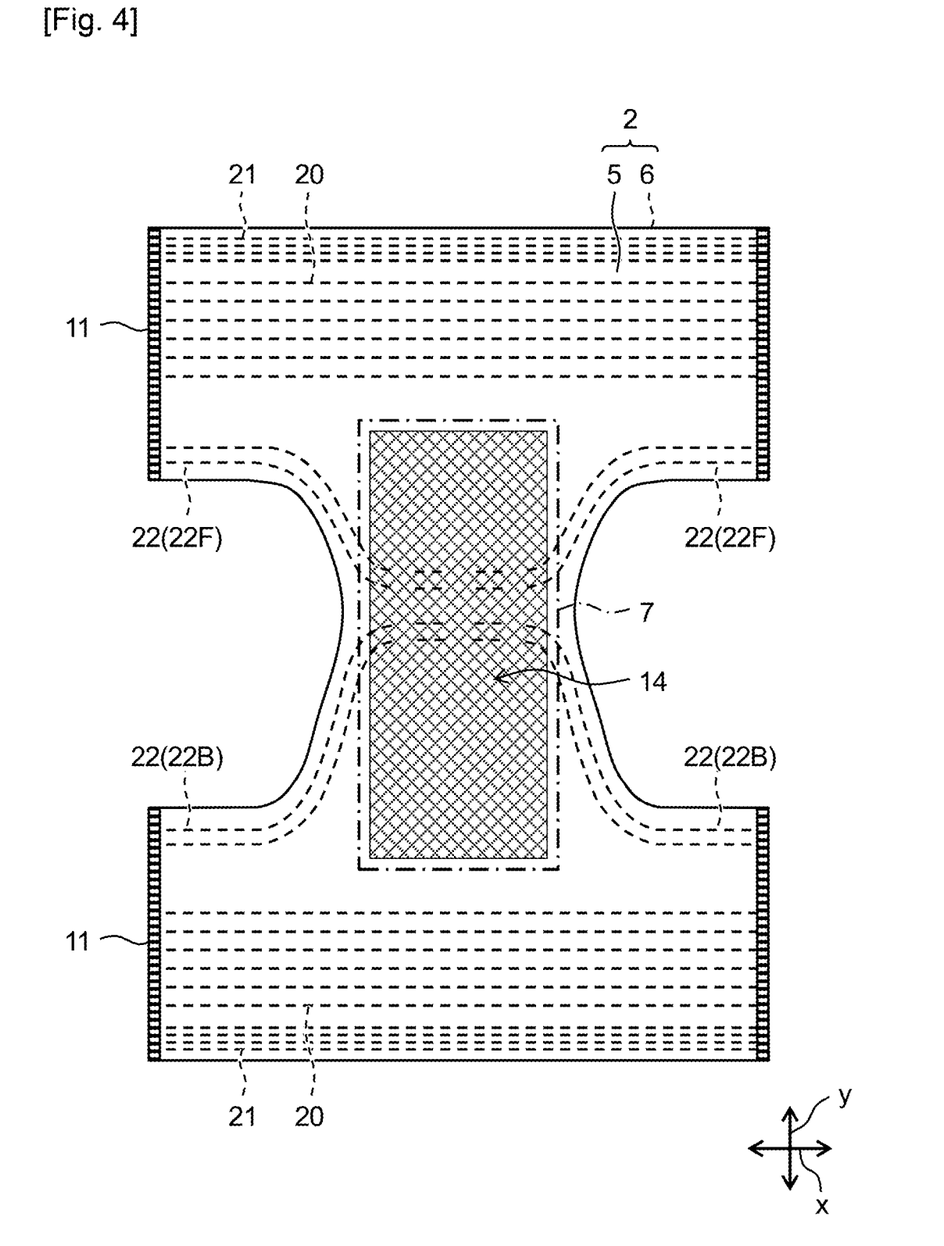
FIG. 4. shows a plan view of an exterior member of the disposable diaper as viewed from a skin-facing side thereof, and shows an example of forming a first adhering region where the absorbent body is adhered to the exterior member.

The absorbent body 7 is adhered to the skin-facing side of the exterior member 2 at a first adhering region. The first adhering region may be provided on the entire surface of the absorbent body 7 on the outer surface side, or may be provided only in a part thereof. FIG. 4 shows a plan view of the exterior member 2 as viewed from the skin-facing side thereof, an outline of the absorbent body 7 provided on the exterior member 2 is indicated by a dashed-dotted line, and the first adhering region 14 where the absorbent body 7 is adhered to the exterior member 2 is indicated by cross-hatching. In the FIG. 4, an example in which the first adhering region 14 is provided on substantially the entire surface of the absorbent body 7 on the outer surface side is shown.

As is described below, the first adhering region 14 is provided so as to overlap with a second adhering region 16 in which the inner sheet 5 and the outer sheet 6 are adhered to each other (specifically, a second front adhering region 16F, a second middle adhering region 16M and a second rear adhering region 16B). The first adhering region 14 may be provided continuously or intermittently in the front-rear direction y, and the first adhering region 14 is preferably provided continuously from a portion which the second front adhering region 16F is overlapped with to a portion which the second rear adhering region 16B is overlapped with. From the viewpoint of stably fixing the absorbent body 7 to the exterior member 2, the first adhering region 14 is preferably provided in a wide range in the front-rear direction y in the absorbent body 7. For example, a length of the first adhering region 14 in the front-rear direction y (in the case where there are a plurality of them, a total length thereof) is preferably 70% or more, preferably 80% or more, even more preferably 90% or more of a length of the absorbent body 7 in the front-rear direction y.

The first adhering region 14 may be provided continuously or intermittently in the width direction x. In the case that the first adhering region 14 is provided intermittently in the width direction x, a first non-adhering region 15 in which the absorbent body 7 is not adhered to the exterior member 2 is formed between the adjacent first adhering regions 14. In this case, it is preferable that the 2 or more and 5 or less, more preferably 4 or less, and even more preferably 3 or less first adhering regions 14 are arranged side by side in the width direction x.

In the case that the first adhering region 14 is provided intermittently in width direction x, a length of the first adhering region 14 in the width direction x (a total length of the plurality of them) is preferably 20% or more, more preferably 30% or more, and preferably 90% or less, more preferably 80% or less, even more preferably 70% or less of a length of the absorbent body 7 in the width direction x. In the case that the first adhering region 14 is provided continuously in the width direction x, the length of the first adhering region 14 in the width direction x is preferably 60% or more, more preferably 70% or more, even more preferably 80% or more of the length of the absorbent body 7 in the width direction x.

In the case that the first adhering region 14 is provided continuously with respect to both the width direction x and the front-rear direction y, the first adhering region 14 is preferably formed in a substantially rectangular shape. In the case that the first adhering region 14 is provided intermittently with respect to the width direction x and/or the front-rear direction y, it is preferable that adhering regions each formed in a substantially rectangular shape are arranged side by side in the width direction x and/or the front-rear direction y, whereby the first adhering region 14 is formed.

Figure 5:
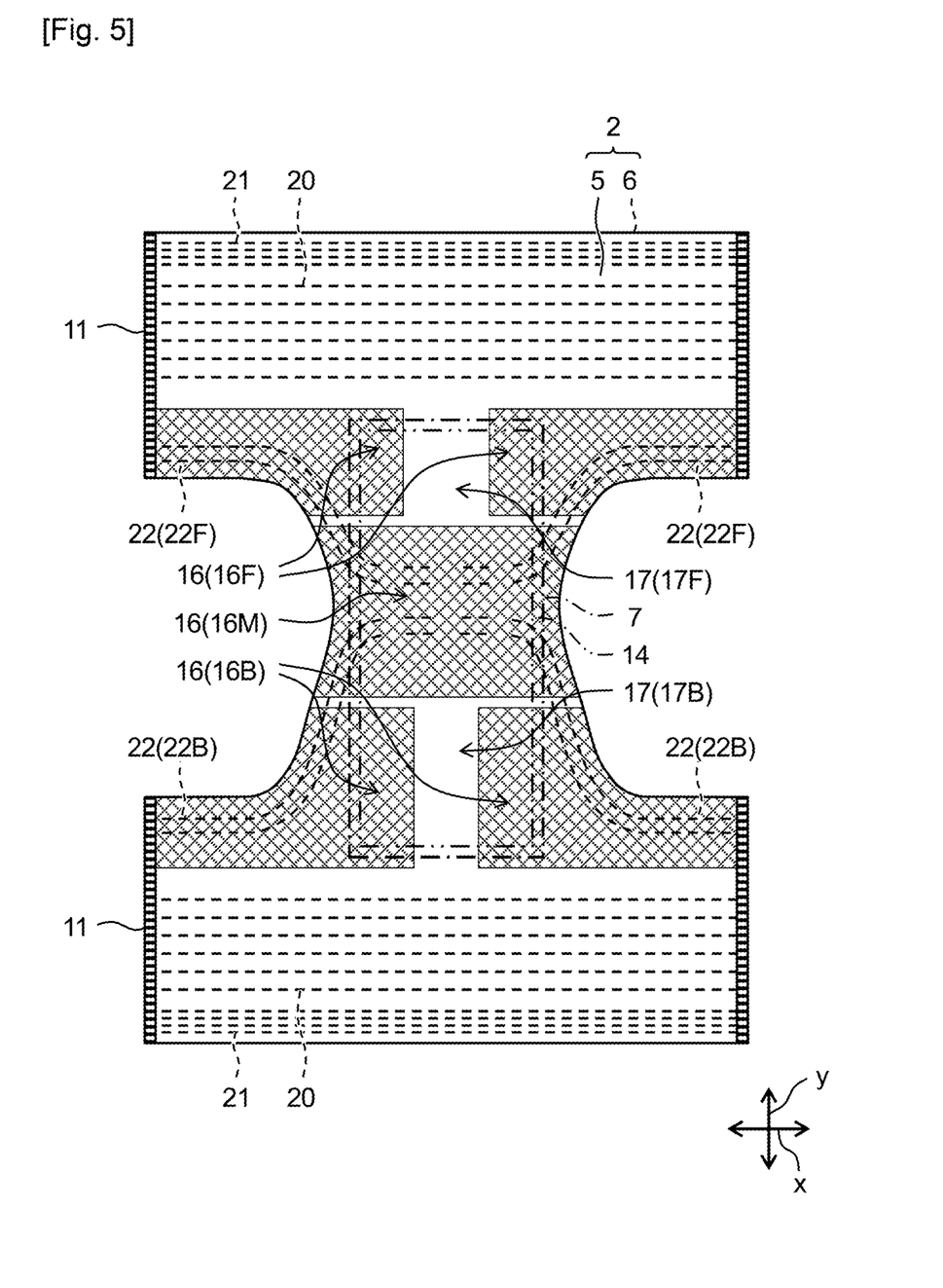
FIG. 5 shows a plan view of the exterior member of the disposable diaper as viewed from the skin-facing side thereof, and shows an example of forming a second adhering region where an inner sheet and an outer sheet of the exterior member are adhered to each other.

In the exterior member 2, the inner sheet 5 and the outer sheet 6 are adhered to each other at the second adhering region 16. FIG. 5 shows a plan view of the exterior member 2 as viewed from the skin-facing side thereof, an outline of the absorbent body 7 provided on the exterior member 2 is indicated by a dashed-dotted line, an outline of the first adhering region 14 is indicated by a dashed-two dotted line, and the second adhering region 16 in which the inner sheet 5 and the outer sheet 6 of the exterior member 2 are adhered to each other is indicated by cross-hatching.

The second adhering region 16 includes a second middle adhering region 16M provided at the crotch part, a second front adhering region 16F located anterior to the second middle adhering region 16M and a second rear adhering region 16B located posterior to the second middle adhering region 16M. The second front adhering region 16F, the second middle adhering region 16M and the second rear adhering region 16B are defined by dividing the exterior member 2 in the front-rear direction y, and are provided so as to extend in the width direction x, respectively.

The second middle adhering region 16M is provided so that at least a part thereof overlaps with the first adhering region 14, and is provided continuously from one side edge to the other side edge, with respect to the width direction x, of the absorbent body 7 at a portion which the absorbent body 7 is overlapped with. In the second middle adhering region 16M, the front leg elastic member 22F and the rear leg elastic member 22B are provided so as to extend across the crotch part R. As the front leg elastic member 22F and the rear leg elastic member 22B extend across the crotch part R in the second middle adhering region 16M, the front leg elastic member 22F and the rear leg elastic member 22B are firmly adhered and fixed to the inner sheet 5 and/or the outer sheet 6 at the portion which the absorbent body 7 is overlapped with. For example, as is described below, in the case that the front leg elastic member 22F and the rear leg elastic member 22B are provided so as to extend intermittently across the crotch part R, an appearance of the diaper can be improved since fragments of the front leg elastic member 22F and the rear leg elastic member 22B are not dispersed.

The second front adhering region 16F is provided on a front side of the second middle adhering region 16M, and is provided such that at least a part thereof overlaps with the first adhering region 14. The second rear adhering region 16B is provided on a rear side of the second middle adhering region 16M, and is provided such that at least a part thereof overlaps with the first adhering region 14. Unlike the second middle adhering region 16M, the second front adhering region 16F and the second rear adhering region 16B are provided intermittently from one side edge to the other side edge, with respect to the width direction x, of the absorbent body at a portion which the absorbent body 7 is overlapped with. As a result, a second front non-adhering region 17F in which the inner sheet 5 and the outer sheet 6 are not adhered to each other is formed at a portion which the absorbent body 7 is overlapped with on a front side of the second middle adhering region 16M and in which the second front adhering region 16F is provided intermittently in the width direction x. In addition, a second rear non-adhering region 17B in which the inner sheet 5 and the outer sheet 6 are not adhered to each other is formed at a portion which the absorbent body 7 is overlapped with on a rear side of the second middle adhering region 16M and in which the second rear adhering region 16B is provided intermittently in the width direction x.

Since the exterior member 2 is configured so that the second front non-adhering region 17F or the second rear non-adhering region 17B are formed at the portion which the absorbent body 7 is overlapped with in this manner, air permeability is increased, and sweat or moisture generated from a wearer is easily discharged to the outside of the diaper. In the disposable diaper 1, air permeability tends to be particularly poor at a portion where the exterior member 2 is overlapped with the absorbent body 7, however, when the second non-adhering region 17 in which the inner sheet 5 and the outer sheet 6 are not adhered to each other is formed at the portion which the absorbent body 7 is overlapped with in the exterior member 2, air permeability at the portion where the exterior member 2 is overlapped with the absorbent body 7 can be improved. In addition, in the case that the back sheet 9 of the absorbent body 7 is moisture permeable, after urine or the like is absorbed by the absorbent body 7, fluid becomes moisture and permeates through the moisture permeable back sheet 9 and further permeates through the second front non-adhering region 17F or the second rear non-adhering region 17B, thereby being preferably discharged to the outside of the diaper.

Here, when the second non-adhering region 17 in which the inner sheet 5 and the outer sheet 6 are not adhered to each other is formed in the exterior member 2 in this manner, there is concern that the absorbent body 7 easily moves at a wearer's crotch and it may be difficult to set it at an intended position when wearing the diaper. Therefore, in the disposable diaper 1, the second middle adhering region 16M is provided continuously from one side edge to the other side edge, with respect to the width direction x, of the absorbent body 7 at a portion which the absorbent body 7 is overlapped with, and the second front adhering region 16F and the second rear adhering region 16B are provided so as to overlap with both the one side edge and the other side edge, with respect to the width direction x, of the first adhering region 14. Thereby, the position of the absorbent body 7 relative to the exterior member 2 is suitably settled in the second middle adhering region 16M, and further in the second front adhering region 16F and the second rear adhering region 16B, the portion of both side portions of the absorbent body 7 relative to the exterior member 2 in the width direction x is suitably settled via the first adhering region 14 and the second adhering region 16, due to the configuration that the one side edge and the other side edge, with respect to the width direction x, of the first adhering region 14 are provided so as to overlap with the second adhering region 16, and as a result, the absorbent body 7 is less likely to shift relative to the exterior member 2 (particularly to the outer sheet 6). Therefore, wearing feeling of the disposable diaper 1 can be improved. In the case where the first adhering region 14 is provided intermittently in the width direction x, the one side edge and the other side edge, with respect to the width direction x, of the first adhering region 14 mean one side edge, with respect to the width direction x, of the first adhering region 14 on the most one side in the width direction x and the other side edge, with respect to the width direction x, of the first adhering region 14 on the most the other side in the width direction x, respectively.

In the disposable diaper 1, both the second front adhering region 16F and the second rear adhering region 16B are preferably provided as described above, however, only the second front adhering region 16F or only the second rear adhering region 16B may be provided as described above.

The second front adhering region 16F is preferably provided so as to extend forward of the front end of the absorbent body 7. Also, the second rear adhering region 16B is preferably provided so as to extend rearward of the rear end of the absorbent body 7. When the second front adhering region 16F or the second rear adhering region 16B is provided in this manner, the position of the end portion of the absorbent body 7 relative to the exterior member 2 in the front-rear direction y is suitably settled, and the absorbent body 7 is less likely to shift relative to the exterior member 2 (particularly to the outer sheet 6) over a wide range in the front-rear direction y.

On the front side of the second front adhering region 16F, it is preferable that a non-adhering region in which the inner sheet 5 and the outer sheet 6 are not adhered to each other is formed adjacent to the second front adhering region 16F. Also, on the rear side of the second rear adhering region 16B, it is preferable that a non-adhering region in which the inner sheet 5 and the outer sheet 6 are not adhered to each other is formed adjacent to the second rear adhering region 16B. And the second front non-adhering region 17F and/or the second rear non-adhering region 17B are preferably connected to these non-adhering regions. Thereby, moisture accumulated in the second front non-adhering region 17F or the second rear non-adhering region 17B is easily discharged to the outside of the diaper.

In the case that the body elastic member 20 is disposed on the front body part P and the rear body part Q of the exterior member 2, it is preferable that the second front adhering region 16F and/or the second rear adhering region 16B is provided apart from the body elastic member 20, and a non-adhering region in which the inner sheet 5 and the outer sheet 6 are not adhered to each other is formed between the second front adhering region 16F and the body elastic member 20 and/or between the second rear adhering region 16B and the body elastic member 20. By providing the non-adhering region in this manner, moisture accumulated in the second front non-adhering region 17F or the second rear non-adhering region 17B is easily discharged to the outside of the diaper.

In the case that the plurality of body elastic members 20 are disposed in the front body part P and the rear body part Q of the exterior member 2, it is preferable that the body elastic members 20 are adhered to the inner sheet 5 and the outer sheet 6, and a non-adhering region in which the inner sheet 5 and the outer sheet 6 are not adhered to each other is formed so as to extend in the width direction x between the adjacent body elastic members 20. Thereby, air permeability of the exterior member 2 can be increased even in the region where the body elastic members 20 are disposed in the front body part P and the rear body part Q.

It is preferable that the second front non-adhering region 17F extends forward of the front end of the absorbent body 7 from the position overlapping the absorbent body 7 on the front side of the second middle adhering region 16M. Similarly, it is preferable that the second rear non-adhering region 17B extends rearward of the rear end of the absorbent body 7 from the position overlapping the absorbent body 7 on the rear side of the second middle adhering region 16M. When the second front non-adhering region 17F and/or the second rear non-adhering region 17B is formed in this manner, moisture accumulated in the second front non-adhering region 17F or the second rear non-adhering region 17B is easily discharged to the outside of the diaper.

It is preferable that the second middle adhering region 16M is provided continuously from one side edge to the other side edge, with respect to the width direction x, of the absorbent body 7 in a portion which the absorbent body 7 is overlapped with and is further provided so as to extend outward in the width direction x from the one side edge and the other side edge, with respect to the width direction x, of the absorbent body 7 to an outer edge of the exterior member 2. By providing the second middle adhering region 16M in this manner, the parts of the front leg elastic member 22F and the rear leg elastic member 22B that cross the crotch part R and extend along the edge of the leg opening 4 are adhered and fixed to the inner sheet 5 and/or the outer sheet 6.

It is preferable that the second front adhering region 16F is provided so as to extend outward in the width direction x from one side edge and the other side edge, with respect to the width direction x, of the absorbent body 7 and overlap with the front leg elastic member 22F. It is also preferable that the second rear adhering region 16B is provided so as to extend outward in the width direction x from one side edge and the other side edge, with respect to the width direction x, of the absorbent body 7 and overlap with the rear leg elastic member 22B. By providing the second front adhering region 16F and/or the second rear adhering region 16B in this manner, the part of the front leg elastic member 22F and/or the rear leg elastic member 22B that extends along the edge of the leg opening 4 is adhered and fixed to the inner sheet 5 and/or the outer sheet 6. In this case, it is preferable that the second front adhering region 16F extends forward of the front leg elastic member 22F, and the second rear adhering region 16B extends rearward of the rear leg elastic member 22B. Thereby, more parts of the front leg elastic member 22F and the rear leg elastic member 22B are adhered and fixed to the inner sheet 5 and/or the outer sheet 6. Forward of the front leg elastic member 22F means forward of the most front end of the front leg elastic member 22F, and rearward of the rear leg elastic member 22B means rearward of the most rear end of the rear leg elastic member 22B. Here, it is preferable that the second front adhering region 16F and/or the second rear adhering region 16B extends to a region within 10 mm (more preferably within 5 mm) inward from the side joint part 11 of the exterior member 2 in the width direction x.

It is preferable that the front leg elastic member 22F and the rear leg elastic member 22B extend intermittently across the crotch part in the second middle adhering region 16M. In other parts, it is preferable that the front leg elastic member 22F and the rear leg elastic member 22B continuously extend. When the front leg elastic member 22F and the rear leg elastic member 22B are provided in this manner, the absorbent body 7 is less likely to be distorted by contraction force of the front leg elastic member 22F and the rear leg elastic member 22B, and fittability of the absorbent body 7 to a wearer's crotch can be improved. For providing the leg elastic member 22 is intermittently, the leg elastic member 22 may be adhered and fixed to the inner sheet 5 and/or the outer sheet 6, followed by cutting the leg elastic member 22 with a cutter or the like. By doing so, the leg elastic member 22 can be easily intermittently disposed in manufacturing, and the contraction force of the elastic member can be substantially lost at a part where the leg elastic member 22 is intermittently disposed.

The length of the second middle adhering region 16M in the front-rear direction y is not particularly limited, as long as the second middle adhering region 16M is provided so as to overlap with both a part of the front leg elastic member 22F that crosses the crotch part R and a part of the rear leg elastic member 22B that crosses the crotch part R. The length of the second middle adhering region 16M in the front-rear direction y is preferably 15% or more, more preferably 20% or more, and even more preferably 25% or more of the length of the absorbent body 7 in the front-rear direction y. In addition, from the viewpoint of securing the length of the second front non-adhering region 17F and the second rear non-adhering region 17B in the front-rear direction y and enhancing air permeability of the exterior member 2, the length of the second middle adhering region 16M in the front-rear direction y is preferably 50% or less, more preferably 45% or less, even more preferably 40% or less of the length of the absorbent body 7 in the front-rear direction y.

The length, with respect of the front-rear direction y, of a part of the second front adhering region 16F or the second rear adhering region 16B that overlaps with the absorbent body 7 is preferably 10% or more, more preferably 15% or more, even more preferably 20% or more, and preferably 50% or less, more preferably 45% or less, even more preferably 40% or less of the length of the absorbent body 7 in the front-rear direction y, respectively.

The lengths of the second front adhering region 16F and the second rear adhering region 16B in the front-rear direction y may be the same or different from each other, however, it is preferable that the length of the second rear adhering region 16B in the front-rear direction y is longer than that of the second front adhering region 16F.

The second front adhering region 16F may be provided in contact with the second middle adhering region 16M, or may be provided apart from that in the front-rear direction y. The second rear adhering region 16B may also be provided in contact with the second middle adhering region 16M, or may be provided apart from that in the front-rear direction y. However, from the viewpoint of enhancing air permeability of the exterior member 2, the second front adhering region 16F and/or the second rear adhering region 16B is preferably provided apart from the second middle adhering region 16M in the front-rear direction y. In this case, a non-adhering region in which the inner sheet 5 and the outer sheet 6 are not adhered to each other is formed at a portion where the second front adhering region 16F or the second rear adhering region 16B is separated from the second middle adhering region 16M, and moisture accumulated in the second front non-adhering region 17F or the second rear non-adhering region 17B is easily discharged to the outside of the diaper through this non-adhering region. The separation distance between the second front adhering region 16F and the second middle adhering region 16M in the front-rear direction y and the separation distance between the second rear adhering region 16B and the second middle adhering region 16M in the front-rear direction y of this case are preferably 2 mm or more, and preferably 20 mm or less, more preferably 15 mm or less, even more preferably 10 mm or less.

The second front adhering region 16F and/or the second rear adhering region 16B is provided intermittently in the width direction x from one side edge to the other side, with respect to the width direction x, of the absorbent body 7 at a portion which the absorbent body 7 is overlapped with, whereby the second front non-adhering region 17F and/or the second rear non-adhering region 17B is formed. At this time, the number of the second front non-adhering regions 17F formed at the portion which the absorbent body 7 is overlapped with is preferably three or less, more preferably two or less, and even more preferably only one. Similarly, the number of the second rear non-adhering regions 17B formed at the portion which the absorbent body 7 is overlapped with is preferably three or less, more preferably two or less, and even more preferably only one.

Figure 6:
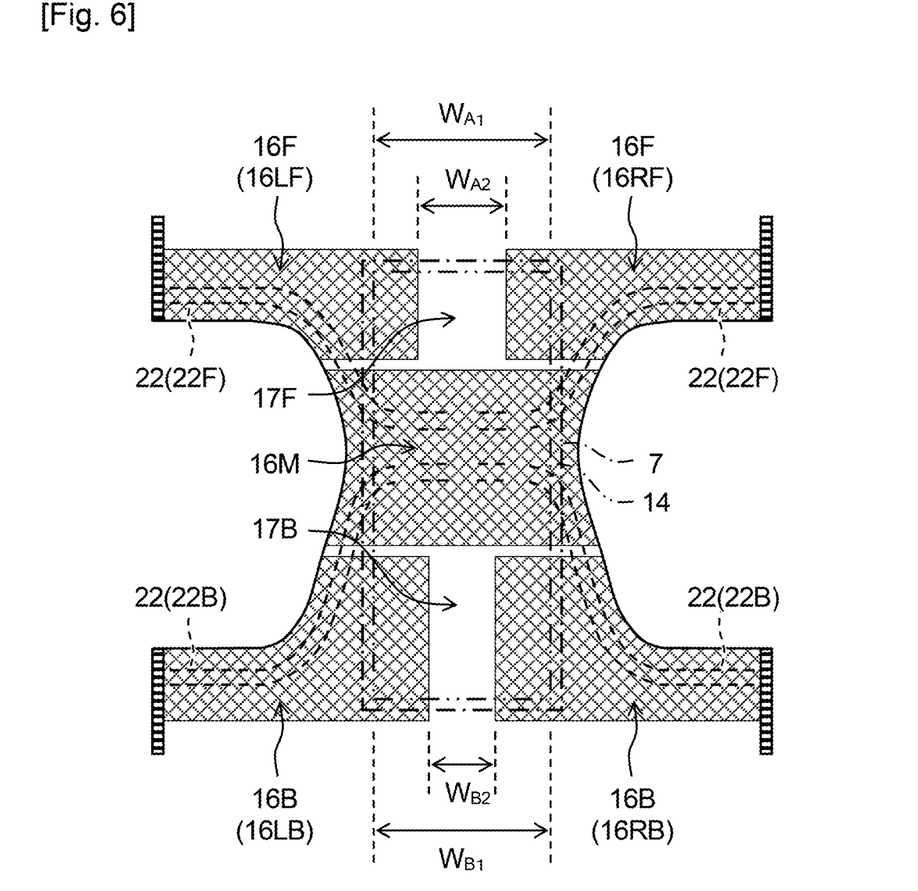
FIG. 6 shows a partial plan view of the exterior member shown in FIG. 5 on the skin-facing side.

A particularly preferable embodiment of the second front adhering region 16F, the second front non-adhering region 17F, the second rear adhering region 16B and the second rear non-adhering region 17B is explained with reference to FIG. 6. FIG. 6 shows a partial plan view of a skin-facing side of the exterior member shown in FIG. 5.

The second front adhering region 16F and the second front non-adhering region 17F are preferably provided as follows. That is, it is preferable that the second front adhering region 16F includes a second right front adhering region 16RF provided on one side in the width direction x and a second left front adhering region 16LF provided on the other side in the width direction x, the right front adhering region 16RF is provided so as to overlap with the one side edge, with respect to the width direction x, of the first adhering region 14, the second left front adhering region 16LF is provided so as to overlap with the other side edge, with respect to the width direction x, of the first adhering region 14, and the second front non-adhering region 17F is formed between the second right front adhering region 16RF and the second left front adhering region 16LF. In this case, it is preferable that the only one second front non-adhering region 17F is formed between the second right front adhering region 16RF and the second left front adhering region 16LF. As a result, an area of the second front non-adhering region 17F can be formed widely to increase the air permeability. In the case that the first adhering region 14 is provided intermittently in the width direction x, the one side edge and the other side edge, with respect to the width direction x, of the first adhering region 14 mean one side edge, with respect to the width direction x, of the first adhering region 14 on the most one side in the width direction x and the other side edge, with respect to the width direction x, of the first adhering region 14 on the most the other side in the width direction x, respectively.

The second rear adhering region 16B and the second rear non-adhering region 17B are preferably provided as follows. That is, it is preferable that the second rear adhering region 16B includes a second right rear adhering region 16RB provided on one side in the width direction x and a second left rear adhering region 16LB provided on the other side in the width direction x, the right rear adhering region 16RB is provided so as to overlap with the one side edge, with respect to the width direction x, of the first adhering region 14, the second left rear adhering region 16LB is provided so as to overlap with the other side edge, with respect to the width direction x, of the first adhering region 14, and the second rear non-adhering region 17B is formed between the second right rear adhering region 16RB and the second left rear adhering region 16LB. In this case, it is preferable that the only one second rear non-adhering region 17B is formed between the second right rear adhering region 16RB and the second left rear adhering region 16LB. As a result, an area of the second rear non-adhering region 17B can be formed widely to increase the air permeability.

The length of the second front non-adhering region 17F in the width direction x (in the case where there are a plurality of them, a total length thereof) and the length of the second rear non-adhering region 17B in the width direction x (in the case where there are a plurality of them, a total length thereof) is preferably 10% or more, more preferably 15% or more of the length of the absorbent body 7 in the width direction x, from the viewpoint of increasing air permeability of the exterior member 2. In addition, from the viewpoint of facilitating the absorbent body 7 to be easily set in an intended position with respect to the exterior member 2 (particularly to the outer sheet 6), the length of the second front non-adhering region 17F in the width direction x and the length of the second rear non-adhering region 17B in the width direction x is preferably 80% or less, more preferably 70% or less of the length of the absorbent body 7 in the width direction x.

With regard to the relationship with the first adhering region 14, the second front non-adhering region 17F and the second rear non-adhering region 17B are preferably provided as follows. That is, as shown in FIG. 6, provided that the length from one side edge to the other side edge, with respect to the width direction x, of a portion where the first adhering region 14 overlaps with the second front adhering region 16F is $W_{A1}$ and the length of the second front non-adhering region 17F in the width direction x (in the case where there are a plurality of them, a total length thereof) is $W_{A2}$, the value of $W_{A2}/W_{A1}$ is preferably 0.15 or more, more preferably 0.20 or more, and preferably 0.90 or less, more preferably 0.80 or less. Similarly, provided that the length from one side edge to the other side edge, with respect to the width direction x, of a portion where the first adhering region 14 overlaps with the second rear adhering region 16B is $W_{B1}$ and the length of the second rear non-adhering region 17B in the width direction x (in the case where there are a plurality of them, a total length thereof) is $W_{B2}$, the value of $W_{B2}/W_{B1}$ is preferably 0.15 or more, more preferably 0.20 or more, and preferably 0.90 or less, more preferably 0.80 or less. Thereby, it becomes easy to set the absorbent body 7 at an intended position with respect to the exterior member 2 (particularly to the outer sheet 6) when wearing the diaper while increasing air permeability of the exterior member 2.

The lengths of the second front non-adhering region 17F and the second rear non-adhering region 17B in the width direction x may be the same or different from each other, however, it is preferable that the length $W_{A2}$ of the second front non-adhering region 17F in the width direction x is longer than the length $W_{B2}$ of the second rear non-adhering region 17B in the width direction x. Thereby, air permeability on the front side of the diaper, in which more urine tends to be collected, can be increased.

For the same reason, it is preferable that an area of the second front non-adhering region 17F is larger than that of the second rear non-adhering region 17B. The area of the second front non-adhering region 17F corresponds to the area of the intermittent portion, with respect to the width direction x, of the second front adhering region 16F, and the area of the second rear non-adhering region 17B corresponds to the area of the intermittent portion, with respect to the width direction x, of the second rear adhering region 16B.

As a specific embodiment of the first adhering region 14 and the second adhering region 16, each adhering region is preferably provided as follows. That is, the first adhering region 14 is preferably provided continuously in the width direction x so as to extend across the plurality of second front adhering regions 16F provided intermittently in the width direction x, and is also preferably provided continuously in the width direction x so as to extend across the plurality of second rear adhering regions 16B provided intermittently in the width direction x. In this manner, when the first adhering region 14 is provided continuously in the width direction x and is provided so as to extend across the plurality of second front adhering regions 16F and/or the second rear adhering regions 16B that is provided intermittently in the width direction x, the absorbent body 7 is less likely to shift relative to the exterior member 2 (particularly to the outer sheet 6) and it becomes easy to set the absorbent body 7 at an intended position at a wearer's crotch when wearing the diaper.

Figure 7:
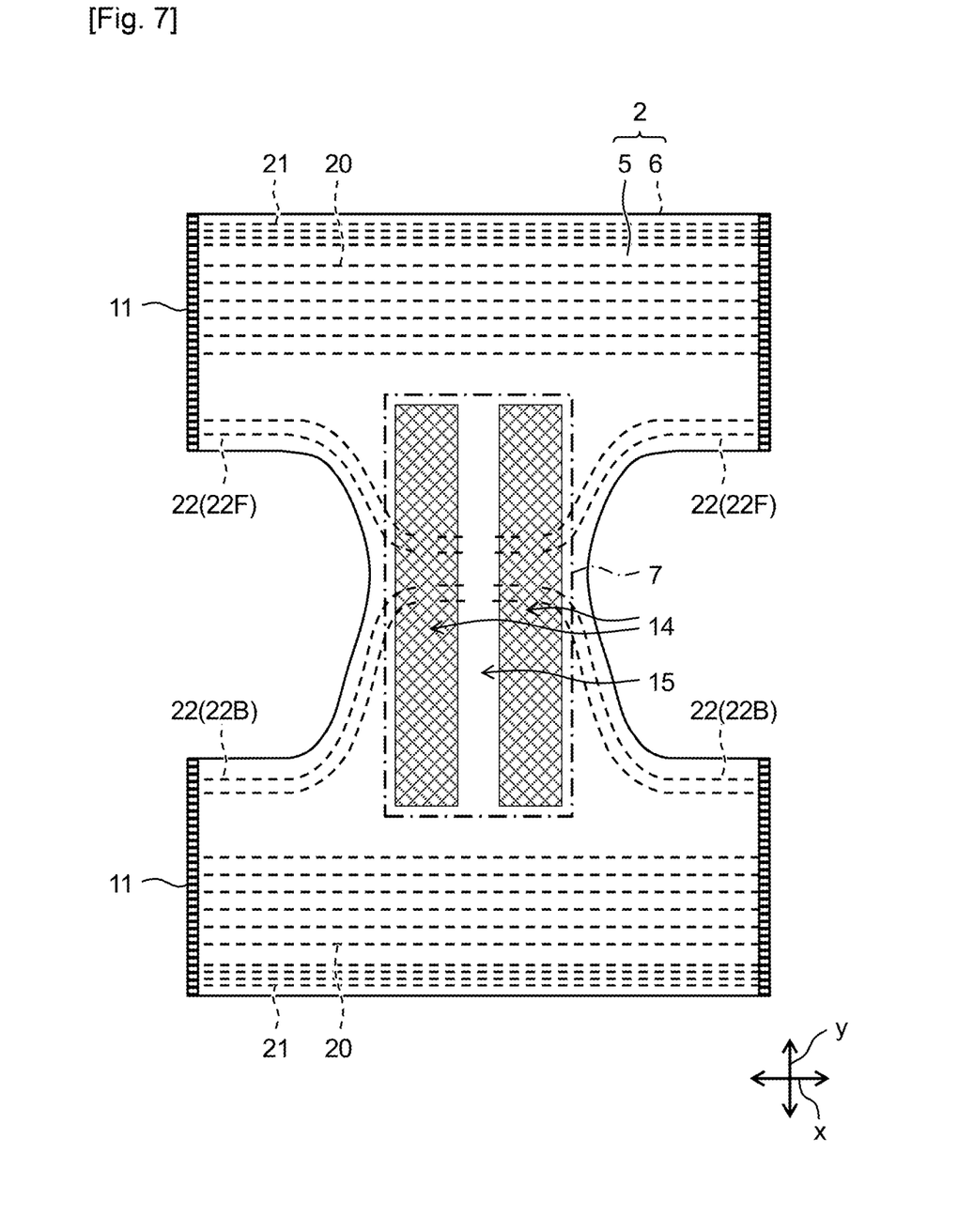
FIG. 7 shows a plan view of the exterior member of the disposable diaper as viewed from the skin-facing side thereof, and shows an example of forming a first adhering region where the absorbent body is adhered to the exterior member.

From the viewpoint of increasing air permeability of the disposable diaper 1, it is also preferable that the first adhering region 14 is provided intermittently in the width direction x, whereby the first non-adhering region 15 in which the absorbent body 7 is not adhered to the exterior member 2 is formed between the adjacent first adhering regions 14, as shown in FIG. 7. In this case it is preferable that the second front non-adhering region 17F and/or the second rear non-adhering region 17B is provided so as to overlap with the first non-adhering region 15. In FIG. 7, an outline of the absorbent body 7 provided on the exterior member 2 is indicated by a dashed-dotted line, and the first adhering region 14 in which the absorbent body 7 is adhered to the exterior member 2 is indicated by cross-hatching. The first adhering region 14 is provided intermittently in the width direction x on the outer side of the absorbent body 7, and the first non-adhering region 15 in which the absorbent body 7 is not adhered to the exterior member 2 is formed between the adjacent first adhering regions 14. When the first adhering region 14 and the first non-adhering region 15 are formed as shown in FIG. 7 and the second adhering region 16 and the second non-adhering region 17 are formed as shown in FIG. 5, the first non-adhering region 15 comes to be formed so as to overlap with the second front non-adhering region 17F and the second rear non-adhering region 17B.

In the case where the first non-adhering region 15 is provided, the length, with respect to the width direction x, of the overlapping portion between the first non-adhering region 15 and the second front non-adhering region 17F or the second rear non-adhering region 17B (in the case where there are a plurality of them, a total length thereof) is preferably 10% or more, more preferably 15% or more, and preferably 80% or less, more preferably 70% or less of the length of the absorbent body 7 in the width direction x.

As an adhesive for forming the first adhering region 14 and the second adhering region 16, it is convenient to use a hot-melt adhesive in manufacturing. As the hot-melt adhesive, for example, rubber adhesives such as natural rubber, butyl rubber and polyisoprene; styrene elastomers such as styrene-isoprene-styrene block copolymer (SIS), styrene-butadiene-styrene block copolymer (SBS), styrene-ethylene-butadiene-styrene block copolymer (SEBS) and styrene-ethylene-propylene-styrene block copolymer (SEPS) are preferably used as a base polymer. Further, the base polymer may be blended with ethylene-vinyl acetate copolymer (EVA); polyester; acrylic elastomer; polyolefin elastomer or the like to adjust the adhesiveness or fluidity. It is also preferable to use an amorphous polyalphaolefin (APAO) such as ethylene-propylene copolymer as a kind of polyolefin elastomer.

For each adhering region, the adhesive may be applied to the entire region thereof, or may be applied in a net pattern, a linear pattern, or a scattered spot pattern. As a method of applying the adhesive, for example, a curtain spray method, an omega coating method, a spiral coating method, a pattern coating method or the like can be used.

The adhesive forming the first adhering region 14 and the adhesive forming the second adhering region 16 may be the same or different from each other. Further, the adhesive forming the second front adhering region 16F, the adhesive forming the second middle adhering region 16M and the adhesive forming the second rear adhering region 16B may be the same or different from each other. From the viewpoint of improving wearing feeling of the disposable diaper 1, it is preferable that the exterior member 2 is formed softly at the crotch part R, and from such a viewpoint, it is preferable that the second front adhering region 16F and/or the second rear adhering region 16B has higher bending resistance than the second middle adhering region 16M. For example, it is preferable that the amount of adhesive applied per unit area in the second middle adhering region 16M is smaller than the amount of adhesive applied per unit area in the second front adhering region 16F and/or the amount of adhesive applied per unit area in the second rear adhering region 16B. Or, as the adhesive forming the second intermediate adhesive region 16M, it is preferable to use an adhesive having a lower cohesive force than the adhesive forming the second front adhesive region 16F and/or the adhesive forming the second rear adhering region 16B.

This application claims priority to Japanese Patent Application No. 2018-193233, filed on Oct. 12, 2018. All of the contents of the Japanese Patent Application No. 2018-193233, filed on Oct. 12, 2018, are incorporated by reference herein.

REFERENCE SIGNS LIST

1: a disposable diaper
2: an exterior member
3: a waist opening
4: a leg opening
5: an inner sheet
6: an outer sheet
7: an absorbent body
8: a top sheet
9: a back sheet
10: an absorber
14: a first adhering region
15: a first non-adhering region
16: a second adhering region, 16F: a second front adhering region, 16M: a second middle adhering region, 16B: a second rear adhering region
17: a second non-adhering region, 17F: a second front non-adhering region, 17B: a second rear non-adhering region
20: a body elastic member
21: a waist elastic member
22: a leg elastic member, 22F: a front leg elastic member, 22B: a rear leg elastic member
P: a front body part
Q: a rear body part
R: a crotch part

The invention claimed is:

1. A disposable diaper comprising:
an exterior member that has a front body part, a rear body part and a crotch part positioned therebetween and is formed into a pants shape having a waist opening and a pair of leg openings by joining the front body part and the rear body part; and
an absorbent body that is provided at least on the crotch part of the exterior member and includes a top sheet, a back sheet and an absorber provided therebetween;
wherein:
the exterior member includes an inner sheet and an outer sheet;
a front leg elastic member extending across the crotch part and along a front side of an edge of the leg opening and a rear leg elastic member extending across the crotch part and along a rear side of the edge of the leg opening are provided between the inner sheet and the outer sheet;
the absorbent body is adhered to a skin-facing side of the exterior member at a first adhering region;
the inner sheet and the outer sheet are adhered to each other at a second adhering region, the second adhering region includes a second middle adhering region provided at the crotch part, a second front adhering region located anterior to the second middle adhering region and a second rear adhering region located posterior to the second middle adhering region, and the front leg elastic member and the rear leg elastic member are disposed so as to extend intermittently across the crotch part in the second middle adhering region;

the second middle adhering region is provided so that at least a part thereof overlaps with the first adhering region and is provided continuously from one side edge to the other side edge of the absorbent body in the width direction; and the second front adhering region is provided so as to satisfy the following requirement A and/or the second rear adhering region is provided so as to satisfy the following requirement B:

Requirement A:

The second front adhering region is provided apart from the second middle adhering region in a front-rear direction;

the second front adhering region is provided so that at least a part thereof overlaps with the first adhering region and is provided intermittently from one side edge to the other side edge, with respect to the width direction, of the absorbent body, whereby a second front non-adhering region in which the inner sheet and the outer sheet are not adhered to each other is formed at a portion which the absorbent body is overlapped with on a front side of the second middle adhering region; and the second front adhering region is provided so as to overlap with one side edge and the other side edge, with respect to the width direction, of the first adhering region, Requirement B:

The second rear adhering region is provided apart from the second middle adhering region in a front-rear direction;

the second rear adhering region is provided so that at least a part thereof overlaps with the first adhering region and is provided intermittently from one side edge to the other side edge, with respect to the width direction, of the absorbent body, whereby a second rear non-adhering region in which the inner sheet and the outer sheet are not adhered to each other is formed at a portion which the absorbent body is overlapped with on a rear side of the second middle adhering region; and the second rear adhering region is provided so as to overlap with one side edge and the other side edge, with respect to the width direction, of the first adhering region.

2. The disposable diaper according to claim 1, wherein the second middle adhering region is provided so as to extend outward in the width direction from the one side edge and the other side edge, with respect to the width direction, of the absorbent body to an outer edge of the exterior member.

3. The disposable diaper according to claim 1, wherein the second front adhering region is provided so as to extend forward of a front end of the absorbent body, and/or the second rear adhering region is provided so as to extend rearward of a rear end of the absorbent body.

4. The disposable diaper according to claim 1, wherein the second front adhering region is provided so as to extend outward in the width direction from the one side edge and the other side edge, with respect to the width direction, of the absorbent body and overlap with the front leg elastic member, and extend forward of the front leg elastic member, and/or the second rear adhering region is provided so as to extend outward in the width direction from the one side edge and the other side edge, with respect to the width direction, of the absorbent body and overlap with the rear leg elastic member, and extend rearward of the rear leg elastic member.

5. The disposable diaper according to claim 1, wherein a body elastic member extending in the width direction is provided between the inner sheet and the outer sheet on the front body part and the rear body part, and the second front adhering region and/or the second rear adhering region is provided apart from the body elastic member, whereby a non-adhering region in which the inner sheet and the outer sheet are not adhered to each other is formed between the second front adhering region and the body elastic member and/or between the second rear adhering region and the body elastic member.

6. The disposable diaper according to claim 1, wherein a value of $W_{A2}/W_{A1}$ is 0.15 or more and 0.90 or less, provided that a length from one side edge to the other side edge, with respect to the width direction, of a portion where the first adhering region overlaps with the second front adhering region is $W_{A1}$ and a length of the second front non-adhering region in the width direction is $W_{A2}$, and/or a value of $W_{B2}/W_{B1}$ is 0.15 or more and 0.90 or less, provided that a length from one side edge to the other side edge, with respect to the width direction, of a portion where the first adhering region overlaps with the second rear adhering region is $W_{B1}$ and a length of the second rear non-adhering region in the width direction is $W_{B2}$.

7. The disposable diaper according to claim 1, wherein a length of the second front non-adhering region in the width direction is longer than a length of the second rear non-adhering region in the width direction.

8. The disposable diaper according to claim 1, wherein the second front adhering region and/or the second rear adhering region has higher bending resistance than the second middle adhering region.

9. The disposable diaper according to claim 1, wherein the first adhering region is provided continuously in the width direction so as to extend across the plurality of second front adhering regions provided intermittently in the width direction, and/or the first adhering region is provided continuously in the width direction so as to extend across the plurality of second rear adhering regions provided intermittently in the width direction.

10. The disposable diaper according to claim 1, wherein the first adhering region is provided intermittently in the width direction, whereby a first non-adhering region in which the absorbent body is not adhered to the exterior member is formed between the adjacent first adhering regions, and the second front non-adhering region and/or the second rear non-adhering region is provided so as to overlap with the first non-adhering region.

11. The disposable diaper according to claim 1, wherein a boundary between the second front adhering region and the second front non-adhering region is formed in a straight line extending in a front-rear direction, and/or a boundary between the second rear adhering region and the second rear non-adhering region is formed in a straight line extending in a front-rear direction.

12. The disposable diaper according to claim 1, wherein the second front adhering region is provided so as to overlap with a front end of the absorbent body, and/or
the second rear adhering region is provided so as to overlap with a rear end of the absorbent body.

* * * * *